United States Patent [19]

Chakerian

[11] Patent Number: Plant 6,824

[45] Date of Patent: May 30, 1989

[54] PLUM TREE, "SWEET DELIGHT"

[76] Inventor: Jonathan P. Chakerian, 266 W. Sycamore, Reedley, Calif. 93654

[21] Appl. No.: 170,451

[22] Filed: Nov. 9, 1987

[51] Int. Cl.[4] ..... A01H 5/00
[52] U.S. Cl. ..... Plt./38
[58] Field of Search ..... Plt./38

*Primary Examiner*—Robert E. Bagwill
*Attorney, Agent, or Firm*—Worrel & Worrel

[57] ABSTRACT

A new and distinct variety of plum tree which is denominated varietally as "Sweet Delight" and which is somewhat similar to the Ray's Hope Plum Tree (U.S. Plant Pat. No. 5,650) with which it is most closely related, the subject variety characterized by producing fruit which have a deep red skin color, yellow-colored flesh and an elliptical form and which further is ripe for commercial harvesting approximately September 8 through September 20 in the San Joaquin Valley of central California.

1 Drawing Sheet

BACKGROUND OF THE NEW VARIETY

The present invention relates to a plum tree which is denominated varietally as "Sweet Delight" and more particularly to such a plum tree that produces fruit which are ripe for commercial harvesting on September 8 through September 20 in the San Joaquin Valley of central California; the instant variety maturing at approximately the same time as the Ray's Hope Plum Tree (U.S. Plant Pat. No. 5,650) with which it is most closely similar with respect to its date of harvest, but which is distinguishable from the Ray's Hope Plum Tree and characterized as to novelty by producing fruit which have an elliptical shape and a semi-clingstone nature, and which further produces foliage which have dimensions that are characteristically smaller than the foliage dimensions of the Ray's Hope Plum Tree.

ORIGIN AND ASEXUAL REPRODUCTION OF THE NEW VARIETY

For decades, the applicant has endeavored to create new and distinct varieties of stone fruit by selecting different species of fruit trees having desirable characteristics and cross pollinating these fruit trees with known varieties of fruit trees which produce stone fruit. The present variety appears to have resulted from such efforts. In this regard, the applicant, in 1978, attempted to cross a Casselman Plum Tree (unpatented) with an unpatented variety of navel orange tree, the cross pollination procedure taking place at the inventor's farm which is located at 269 W. Sycamore Avenue in Reedley, Calif. It should be understood that the inventor did not employ any procedures which would have effectively inhibited either the presence or introduction of other pollen into the immediate vicinity of the test tree and therefore it is conceivable that an unintentional crossing of a Casselman Plum Tree with a Casselman Plum Tree resulted; or alternatively a chance mutation may have occurred. In any event, the test tree produced several seeds which the inventor later successfully germinated and grew at his same ranch to an extent sufficiently mature to determine that the offspring had noteworthy characteristics. The applicant thereafter asexually reproduced the new and distinct variety by removing bud wood from the original offspring and grafting it onto Nemagard root stock. This first asexual reproduction occurred in 1980 at the applicant's same ranch which is located near Reedley, Calif. The inventor has continually observed the subsequent offspring produced from this first asexual reproduction and it has been determined that the progeny produced are identical to the original offspring.

SUMMARY OF THE NEW VARIETY

The Sweet Delight Plum Tree is characterized as to novelty by producing fruit which are mature for commercial harvesting approximately September 8 through September 20 in the San Joaquin Valley of central California, the date of ripening occurring approximately five weeks later than the Casselman Plum Tree (unpatented) and approximately three weeks earlier than the Roysum Plum Tree (U.S. Plant Pat. No. 2,619) with which it is somewhat closely related. The subject variety is further similar in date of harvesting with respect to the Ray's Hope Plum Tree (U.S. Plant Pat. No. 5,650), but is distinguishable therefrom and further characterized as to novelty by producing fruit which have an elongated shape, a smaller leaf size, and are semi-clingstone by nature.

BRIEF DESCRIPTION OF THE DRAWINGS

The accompanying drawing is a color photograph of a twig bearing typical leaves showing the dorsal and ventral coloration thereof; four plums showing their coloration sufficiently matured for harvesting and shipment; and one plum halved transversely of the suture plane to illustrate the flesh and stone coloration, all of the subject variety.

DETAILED DESCRIPTION

Referring more specifically to the pomological details of this new and distinct variety of Plum Tree, the following has been observed under the ecological conditions prevailing at the farm of the inventor which is located in Reedley, Calif. All major color code designations are by reference to the "Dictionary of Color", by Maerz and Paul, Second Edition, published in 1950. However, common color names are also employed occasionally.

TREE

Size:

*Generally.*—Average. Vigor: Vigorous. Figure: Upright, dense, and vase formed; the shape and density of the subject tree being determined by pruning practices.

Productivity: Very productive.

Regularity of bearing: Regular; the variety appears to be self pollinating.

Trunk:

*Size.*—Average.

*Texture.*—Smooth.

Branches:

*Size.*—Average.

*Texture.*—Regular plum bark.

Lenticels: Average in size and numbers.

LEAVES

Size:

*Generally.*—Medium to small.

*Length.*—Variable, 6.5 to 9.8 cm.; average length approximately 8.3 cm.

*Width.*—Variable, 2.5 to 4.2 cm.; average width approximately 3.3 cm.

Form: Oval or somewhat elliptical; acutely pointed.

*Leaf base.—form:*—Acute to acuminate.

*Leaf tip:—form.—Acute.*

Thickness: Thin.

Color:

*Dorsal surface.*—Medium to dark green, (Plate 24, L-3 Page 71).

*Ventral surface.*—Light green, (Plate 21, I-2 Page 65).

Texture: Smooth.

Marginal form: Finely serrate.

Petiole:

*Length.*—Short, approximately 16.8 mm.

*Thickness.*—Slender, approximately 1.5 mm.

Leaf glands: None evident.

Flowers:

*Date of full bloom.*—Seven or eight days later than the Casselman Plum Tree (unpatented), or the Santa Rosa Plum Tree (unpatented) in the San Joaquin Valley of central California.

*Size.*—Medium. The petals of the subject variety are somewhat slightly smaller than the petals produced by the Casselman Plum Tree.

*Colors.*—A white-yellow, the color is not distinctive of the subject variety.

Flower buds:

*Generally.*—Tender.

*Size.*—Small and short.

*Form.*—Pointed and slightly appressed.

*Pubescent.*—Scant or none.

FRUIT

Maturity when described: Ripe for commercial harvesting and shipment approximately September 8 through September 20; it should be understood that harvesting will be conducted when the sugar level in the subject variety reaches a level of 19% through 21.5%, by weight.

Size:

*Generally.*—Uniform; medium to small.

*Diameter in the axial plane.*—Approximately 54.1 mm.

*Diameter transverse in the suture plane.*—Approximately 49.2 mm.

*Diameter transverse in the cheek plane.*—Approximately 51.3 mm.

Form:

*Generally.*—Uniform and symmetrical. The variety has a noteworthy elliptical shape. This characteristic is clearly illustrated in the drawing.

Suture:

*Generally.*—The suture appears as a distinct and shallow line which extends from the base but discontinues at the apex; furthermore, the suture is a shallow but distinct line that extends from the cavity, (at the fruit stem) to the apex.

Ventral surface:

*Shape.*—Rounded slightly; the lips are equal.

Cavity:

*Generally.*—Flaring, and elongated in the suture plane with the suture appearing on one side.

*Depth.*—Approximately 3.9 mm.

*Breadth.*—Approximately 6.9 mm.

*Markings.*—None are evident.

Base:

*Shape.*—Rounded to slightly truncate.

Apex:

*Form.*—Rounded and very slightly depressed.

Pistil point:

*Position.*—Apical.

Skin:

*Thickness.*—Medium to thin.

*Texture.*—Tender.

Tenacious to flesh: Yes.

Tendency to crack: Not evident in the dry season.

Down: Wanting.

Skin color: Dark red, (Plate 8, L-4, Page 39).

Bloom: Heavy.

Flesh color: Yellow, (Plate 10, F-7, Page 43).

Surface of pit cavity:

*Color.*—Yellow, closely similar to the surrounding flesh coloration.

Amygdalin: Wanting.

Texture: Firm, fine and crisp.

Fibers: Few, fine and tender.

Ripening: Even.

Flavor: Subacid, and delicate.

Aroma: Wanting.

Eating quality: Good.

STONE

Generally: Variable, semi-freestone, to clingstone; the stone of the subject variety adheres to the flesh along both dorsal and ventral edges.

Fibers:

*Generally.*—Short.

Stone size:

*Generally.*—Medium.

Length: Approximately 22.8 mm.

Breadth: Approximately 15.7 mm.

Thickness: Approximately 8.4 mm.

Form: Variable, oval to ovate.

Base: Straight.

Hilum: Narrow and oval.

Apex:

*Position.*—Acute.

Sides:

*Generally.*—Equal; the sides are slightly curved on both the right and left side.

Surface: Ridged throughout.

Ventral edge: Thick with wings throughout.

Dorsel edge: Narrow.

Color of stone: Dark brown, (Plate 15, A-9 Page 53).

Tendency to split: Not evident in the dry season.

Use: Fresh market and dessert.

Keeping quality: Good.

Resistance to insects and disease: No particular susceptibilities noted.

Shipping quality: Average.

Storage characteristics: Noteworthy: the variety can be stored for periods in excess of six weeks with no deleterious effects noted.

Although the new variety of plum tree possesses the described characteristics as a result of the growing conditions prevailing in Fresno County, Calif., in the central part of the San Joaquin Valley, it is to be understood that variations in the usual magnitude and characteristics incident to growing conditions, fertilization, pruning and pest control are to be expected.

Having thus described and illustrated my new variety of plum tree, what is claimed as new and desired to be secured by Letters Patent is:

1. A new and distinct variety of plum tree substantially as illustrated and described which is somewhat similar to the Ray's Hope Plum Tree (U.S. Plant Pat. No. 5,650) with which it is most closely related with respect to its date of harvesting, but from which it is distinguished as to novelty by bearing fruit which are average in size, uniform, and elliptical in shape, the fruit ripening for commercial harvesting approximately September 8 through September 20 and which further has foliage which have dimensions substantially smaller than the foliage produced by the Ray's Hope Plum Tree.

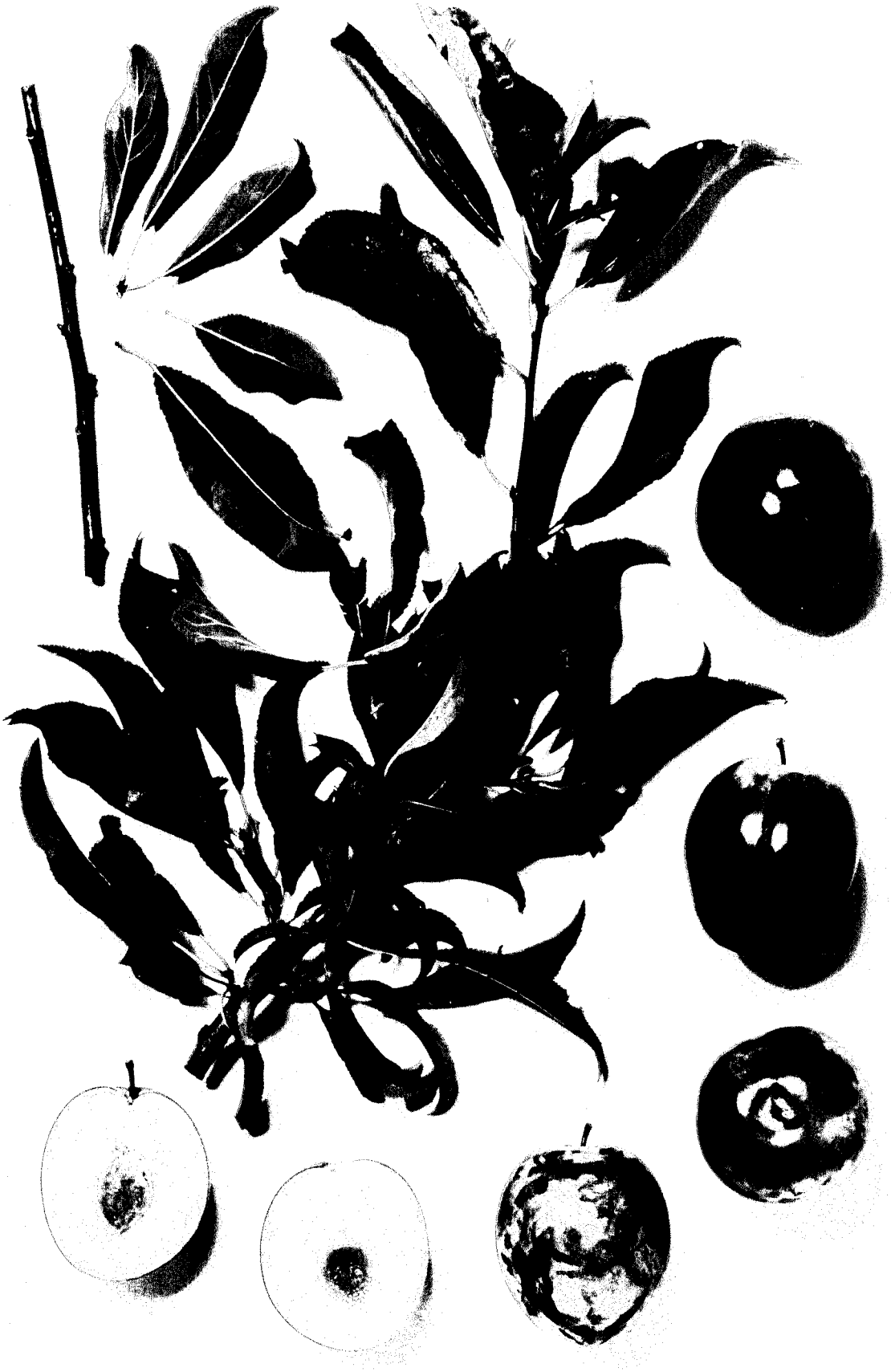

* * * * *